(12) United States Patent
Urakawa et al.

(10) Patent No.: US 9,537,574 B2
(45) Date of Patent: Jan. 3, 2017

(54) OPTICAL TRANSMITTING AND RECEIVING UNIT

(71) Applicant: OLYMPUS CORPORATION, Tokyo (JP)

(72) Inventors: Tsutomu Urakawa, Hachioji (JP); Susumu Kawata, Hachioji (JP); Hideaki Kinouchi, Musashino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/086,553

(22) Filed: Mar. 31, 2016

(65) Prior Publication Data

US 2016/0211919 A1 Jul. 21, 2016

Related U.S. Application Data

(63) Continuation of application No. PCT/JP2015/058123, filed on Mar. 18, 2015.

(30) Foreign Application Priority Data

Sep. 25, 2014 (JP) ................................. 2014-195230

(51) Int. Cl.
*H04B 10/00* (2013.01)
*H04B 10/40* (2013.01)
(Continued)

(52) U.S. Cl.
CPC ........... *H04B 10/40* (2013.01); *A61B 1/00013* (2013.01); *A61B 1/00165* (2013.01); *G02B 6/42* (2013.01); *G02B 23/24* (2013.01); *H04B 10/80* (2013.01)

(58) Field of Classification Search
CPC ....... H04B 10/40; H04B 10/50; H04B 10/503; H04B 10/60; H04B 10/66; H04B 10/67; G02B 6/4248; G02B 6/4251; G02B 6/4255; G02B 6/4256; G02B 6/4262
See application file for complete search history.

(56) References Cited

U.S. PATENT DOCUMENTS

2012/0071019 A1* 3/2012 Takamatsu ........... G02B 6/3821
439/370

FOREIGN PATENT DOCUMENTS

JP 02-033114 A 2/1990
JP 06-181359 A 6/1994
(Continued)

*Primary Examiner* — Daniel Dobson
(74) *Attorney, Agent, or Firm* — Scully, Scott, Murphy & Presser, P.C.

(57) ABSTRACT

An optical transmitting and receiving unit includes: an optical transmitting module having a light emitting element and having a metal case that stores the light emitting element; an optical connector having a ferrule for holding an optical fiber and having a flange portion provided at one end of the ferrule, the ferrule being inserted into a sleeve of the metal case to connect the optical connector with the optical transmitting module; and a tubular waterproof cap that has a bottom, with one end open and the other end closed, and caps the optical connector to seal an optical connecting portion between the optical connector and the optical transmitting module in a watertight manner. The metal case has step portions with different outside diameters. One of the step portions closest to the optical connecting portion contacts an inner surface of the waterproof cap along an entire circumference thereof.

8 Claims, 4 Drawing Sheets

(51) Int. Cl.
*G02B 6/42* (2006.01)
*G02B 23/24* (2006.01)
*H04B 10/80* (2013.01)
*A61B 1/00* (2006.01)
*H04J 14/00* (2006.01)

(56) References Cited

FOREIGN PATENT DOCUMENTS

| | | |
|---|---|---|
| JP | 2000-047066 A | 2/2000 |
| JP | 2004-264543 A | 9/2004 |
| JP | 2007-304266 A | 11/2007 |
| JP | 2010-117440 A | 5/2010 |
| JP | 2010-117443 A | 5/2010 |
| JP | 2012-068323 A | 5/2012 |

\* cited by examiner

OPTICAL TRANSMITTING AND RECEIVING UNIT

CROSS-REFERENCE TO RELATED APPLICATIONS

This application is a continuation of PCT international application Ser. No. PCT/JP2015/058123 filed on Mar. 18, 2015 which designates the United States, incorporated herein by reference, and which claims the benefit of priority from Japanese Patent Application No. 2014-195230, filed on Sep. 25, 2014, incorporated herein by reference.

BACKGROUND

1. Technical Field

The disclosure relates to an optical transmitting and receiving unit with excellent waterproof properties.

2. Related Art

Conventionally, in the medical field, an endoscope system is used when the internal organs of a subject such as a patient are observed. The endoscope system includes, for example, an endoscope having an insertion unit that is provided with an image sensor at its distal end, has a flexible elongated shape, and is inserted into a subject's body cavity; and a processing device that is connected to the insertion unit through a cable or a connector to perform image processing of an in-vivo image captured by the image sensor, and displays the in-vivo image on a display device.

In recent years, an image sensor with a large number of pixels that allows observation of clearer images has been developed, and use of the image sensor with a large number of pixels in an endoscope has been considered. In addition, in consideration of ease of insertion into a subject's body, a reduction in the diameter of the insertion unit is sought. Furthermore, in order to transmit large-volume signals at high speed between the image sensor and the processing device while achieving a reduction in the diameter of the insertion unit, an optical transmitting and receiving unit that transmits signals using an optical fiber is also adopted in the endoscope system.

In the optical transmitting and receiving unit using an optical fiber, if contamination is attached to a distal end face of the optical fiber, there is a possibility of optical loss. Accordingly, there are disclosed an optical fiber connector cap that cleans the distal end face of the optical fiber and an optical fiber connector cap that prevents the adhesion of contamination (see, for example, Japanese Patent Application Laid-open No. 2010-117440 and Japanese Patent Application Laid-open No. 2010-117443).

SUMMARY

In some embodiments, an optical transmitting and receiving unit includes: an optical transmitting and receiving module having a light emitting element or a light receiving element and having a metal case that stores the light emitting element or the light receiving element; an optical connector having a ferrule for holding an optical fiber and having a flange portion provided at one end of the ferrule, the ferrule being inserted into a sleeve of the metal case to connect the optical connector with the optical transmitting and receiving module; and a tubular waterproof cap that has a bottom, with one end open and the other end closed, and caps the optical connector to seal an optical connecting portion between the optical connector and the optical transmitting and receiving module in a watertight manner. The metal case has a plurality of step portions with different outside diameters. One of the plurality of step portions closest to the optical connecting portion contacts an inner surface of the waterproof cap along an entire circumference thereof.

In some embodiments, an optical transmitting and receiving unit includes: an optical transmitting and receiving module having a light emitting element or a light receiving element and having a metal case that stores the light emitting element or the light receiving element; an optical connector having a ferrule for holding an optical fiber and having a flange portion provided at one end of the ferrule, the ferrule being inserted into a sleeve of the metal case to connect the optical connector with the optical transmitting and receiving module; and a tubular waterproof cap that has a bottom, with one end open and the other end closed, and caps the optical connector to seal an optical connecting portion between the optical connector and the optical transmitting and receiving module in a watertight manner. The metal case has a plurality of step portions with different outside diameters. An O-ring is provided in a groove portion closest to the optical connecting portion. The O-ring contacts an inner surface of the waterproof cap along an entire circumference thereof.

The above and other features, advantages and technical and industrial significance of this invention will be better understood by reading the following detailed description of presently preferred embodiments of the invention, when considered in connection with the accompanying drawings.

DETAILED DESCRIPTION

As modes for carrying out the present invention (hereinafter, referred to as "embodiment(s)"), endoscope systems will be described below. The invention is not to be limited by the embodiments. The same reference signs are used to designate the same elements throughout the drawings.

First Embodiment

Figure 1:
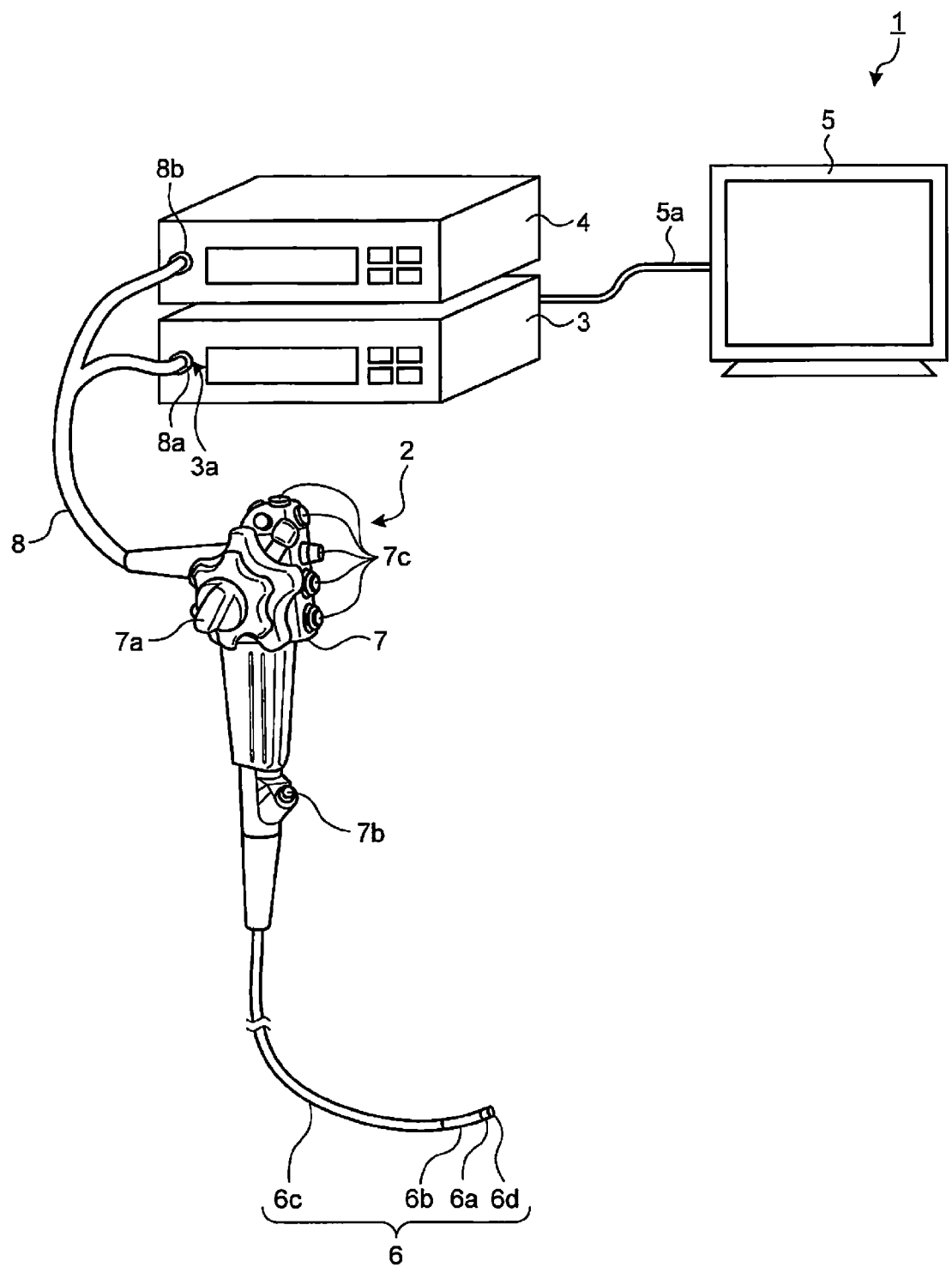
FIG. 1 is a schematic diagram illustrating a configuration of an endoscope system according to a first embodiment of the present invention.

FIG. 1 is a schematic diagram illustrating a configuration of an endoscope system according to embodiments of the present invention. As illustrated in FIG. 1, an endoscope system 1 according to the embodiments includes: an endoscope 2 that is configured to be inserted into a subject's body to image the inside of the subject's body and generate an image signal of the inside of the subject's body; a processing device 3 that is configured to perform predetermined image processing on the image signal generated by the endoscope 2, and to control each element of the endoscope system 1; a light source device 4 that is configured to generate illumination light for the endoscope 2; and a display device 5 that is configured to display, as an image, the image signal having been subjected to the image processing by the processing device 3.

The endoscope 2 includes an insertion unit 6 which is inserted into the subject's body; an operating unit 7 which is on the proximal end portion side of the insertion unit 6 and which is held by an operator; and a flexible universal cord 8 extending from the operating unit 7.

The insertion unit 6 is implemented by an illumination fiber (light guide cable), an electrical cable, an optical fiber, and the like. The insertion unit 6 includes: a distal end portion 6a having an imaging unit including an image sensor to image the inside of the subject's body; a bendable bending portion 6b formed by a plurality of bending pieces; and a flexible tube portion 6c having flexibility and provided on the side of the proximal end portion of the bending portion 6b. The distal end portion 6a includes: an illumination unit configured to illuminate the inside of the subject's body through an illumination lens; an observation unit configured to image the inside of the subject's body; an opening portion 6d communicating with a treatment tool channel; and an air and water supply nozzle (not illustrated).

The operating unit 7 includes a bend knob 7a that allows the bending portion 6b to bend in an up-down direction and a left-right direction; a treatment tool insertion unit 7b into which a treatment tool, such as biopsy forceps or a laser knife which is inserted into a subject's body cavity, is configured to be inserted; and a plurality of switch units 7c that operate peripheral devices such as the processing device 3, the light source device 4, an air supply device, a water supply device, and a gas supply device. A treatment tool is inserted into the treatment tool insertion unit 7b and comes out of the opening portion 6d at a distal end of the insertion unit 6 through the treatment tool channel provided inside.

The universal cord 8 is formed using an illumination fiber, an electrical cable, an optical fiber, and the like. The universal cord 8 is branched at its proximal end, and one of the branched end portions is a connector 8a and the other proximal end is a connector 8b. The connector 8a is removable from a connector 3a of the processing device 3. The connector 8b is removable from the light source device 4. The universal cord 8 propagates illumination light exiting from the light source device 4 to the distal end portion 6a through the connector 8b, the operating unit 7, and the flexible tube portion 6c. The universal cord 8 transmits an image signal captured by the imaging unit included in the distal end portion 6a, to the processing device 3 by an optical transmitting unit which will be described later.

The processing device 3 performs predetermined image processing on the image signal of the inside of the subject's body which is captured by the imaging unit included in the distal end portion 6a of the endoscope 2. The processing device 3 controls the components of the endoscope system 1, based on various types of instruction signals which are transmitted through the universal cord 8 from the switch units 7c included in the operating unit 7 of the endoscope 2.

The light source device 4 is formed using a light source that emits light, a condenser lens, etc. Under control of the processing device 3, the light source device 4 emits light from the light source and supplies the light to the endoscope 2 connected thereto through the connector 8b and the illumination fiber of the universal cord 8, as illumination light for the inside of the subject's body which is a subject for imaging.

The display device 5 is formed using, for example, a display using liquid crystal or an organic EL (Electro Luminescence). The display device 5 displays various types of information including the image having been subjected to the predetermined image processing by the processing device 3, through an image cable 5a. Thus, the operator can observe a desired position of the inside of the subject's body and determine properties by operating the endoscope 2 while viewing the image (in-vivo image) displayed on the display device 5.

Figure 2:
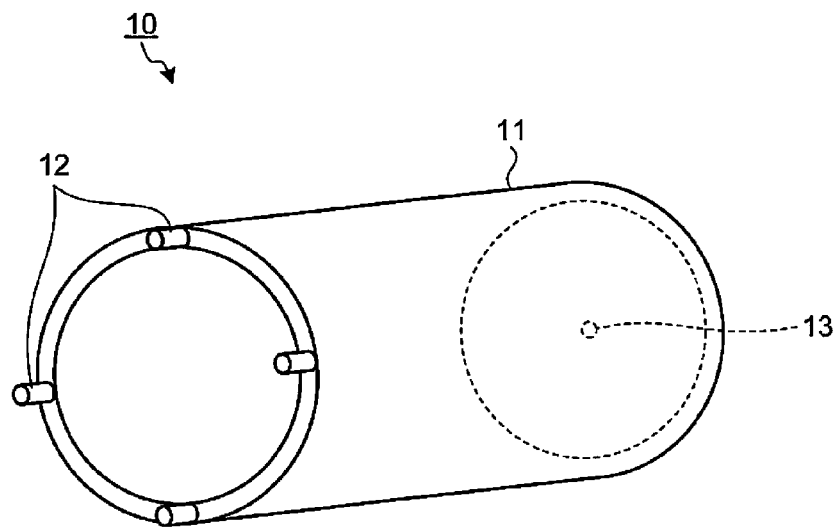
FIG. 2 is a perspective view of a waterproof cap which is used in the endoscope system illustrated in FIG. 1.
Figure 3:
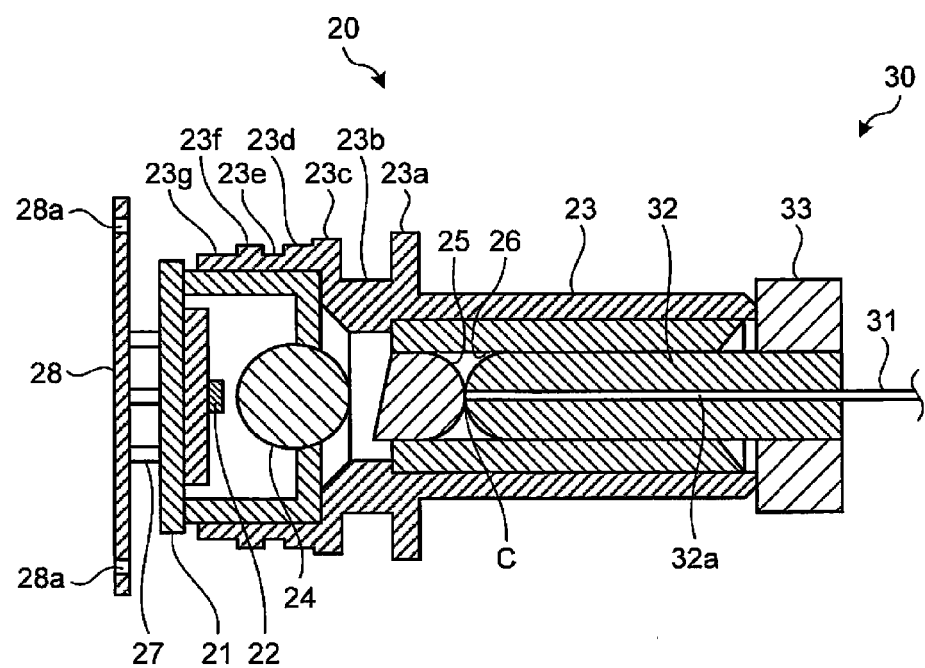
FIG. 3 is a cross-sectional view of an optical transmitting module which is used in the endoscope system illustrated in FIG. 1.
Figure 4:
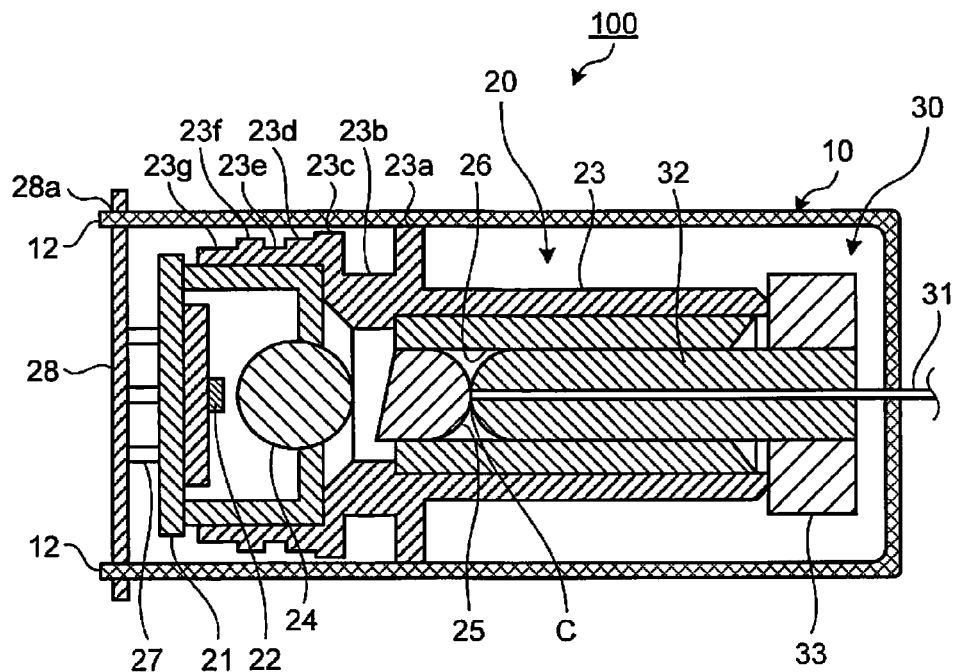
FIG. 4 is a cross-sectional view of an optical transmitting unit in which the optical transmitting module of FIG. 3 is capped by the waterproof cap of FIG. 2.

Next, reference will be made to an optical transmitting unit that transmits the image signal captured by the imaging unit in the endoscope 2 illustrated in FIG. 1 to the processing device 3. FIG. 2 is a perspective view of a waterproof cap which is used in the endoscope system illustrated in FIG. 1. FIG. 3 is a cross-sectional view of an optical transmitting module which is used in the endoscope system illustrated in FIG. 1. FIG. 4 is a cross-sectional view of an optical transmitting unit in which the optical transmitting module of FIG. 3 is capped by the waterproof cap of FIG. 2.

In the first embodiment, an optical transmitting unit 100 includes an optical transmitting module 20; an optical connector 30 connected to the optical transmitting module 20; and a waterproof cap 10 that seals an optical connecting portion between the optical connector 30 and the optical transmitting module 20 in a watertight manner. The optical transmitting unit 100 is disposed at the operating unit 7 or the insertion unit 6 of the endoscope 2, and transmits an optical signal which is obtained by photoelectrically converting an image signal, to the processing device 3 through an optical fiber 31 in the universal cord 8.

As illustrated in FIG. 2, the waterproof cap 10 includes a tubular main body portion 11 having a bottom, with one end open and the other end closed in a height direction; connecting portions 12 on the opening portion side which are connected to a flexible substrate 28 of the optical transmitting module 20 which will be described later; and a hole portion 13 through which the optical fiber 31 is inserted. The main body portion 11 has a cylindrical shape with substantially the same diameter from the opening portion to the bottom.

The optical transmitting module 20 includes: the flexible substrate 28; a light emitting element 21 which is mounted on the flexible substrate 28 through leads 27; and a metal case 23 that stores the light emitting element 21. An image signal captured by the imaging unit is transmitted to the light emitting element 21 through the flexible substrate 28, and photoelectrically converted, and then exits as an optical signal from a light emitting portion 22. The optical signal exiting from the light emitting portion 22 is condensed by a transparent glass body 24 and a condenser lens 25. The metal case 23 includes a sleeve 26 into which a ferrule 32 of the optical connector 30 which will be described later is inserted. In addition, the flexible substrate 28 is provided with hole portions 28a into which the connecting portions 12 of the waterproof cap 10 are inserted. By inserting the connecting portions 12 into the hole portions 28a to connect the waterproof cap 10 to the flexible substrate 28, the strength of a connecting portion between the flexible substrate 28 and the light emitting element 21 through the leads 27 can be improved. Fixation between the connecting portions 12 and the hole portions 28a may be done by press-fitting the connecting portions 12 which are formed to be larger in diameter than the hole portions 28a or, in addition to that, the connecting portions 12 and the hole portions 28a may be fixed by bonding with an adhesive or the like.

The optical connector 30 includes the ferrule 32 that holds the optical fiber 31; and a flange portion 33 provided at one end of the ferrule 32. In the substantially cylindrical ferrule 32, a small hole 32a is provided to pass through the center in an axial direction of the cylindrical shape. By inserting the optical fiber 31 through the small hole 32a, the optical connector 30 holds the optical fiber 31. In this description, an end face of the optical fiber 31 that is inserted through the small hole 32a and that is exposed to an end face of the ferrule 32 on a side inserted into the sleeve 26 (hereinafter, referred to as "distal end portion") is polished in order to reduce loss in the amount of light at the optical connecting portion. The flange portion 33 having a columnar shape concentric with the ferrule 32 is provided at an outer portion of the ferrule 32 on the opposite side of the distal end portion of the ferrule 32 (hereinafter, referred to as "proximal end portion").

A plurality of step portions 23a, 23b, 23c, 23d, 23e, 23f, and 23g are formed on an outer portion of a portion of the metal case 23 where the light emitting element 21 is accommodated. The step portions 23a, 23b, 23c, 23d, 23e, 23f, and 23g form concentric shapes. The optical connecting portion between the optical transmitting module 20 and the optical connector 30, i.e., the step portion 23a that is the closest step portion to an optical connecting portion C between the condenser lens 25 and the ferrule 32, is formed to be larger in outside diameter than the other step portions 23b, 23c, 23d, 23e, 23f, and 23g. As illustrated in FIG. 4, the step portion 23a having the largest outside diameter contacts the inner surface of the waterproof cap 10 along an entire circumference thereof, and functions as waterproof means for ensuring the water-tightness of the optical connecting portion C. In addition, in order to ensure the water-tightness of the optical connecting portion C, it is preferred that a gap between the optical fiber 31 and the hole portion 13 through which the optical fiber 31 is inserted be filled with an adhesive or the like. Alternatively, without using an adhesive, a thermoplastic material or a material that is softened by ultraviolet radiation may be used as a material for the waterproof cap 10 or a covering of the optical fiber 31, and an area around the hole portion 13 may be heated or subjected to ultraviolet irradiation for melt fixation.

Although in the first embodiment the step portion 23a that is the closest to the optical connecting portion C between the condenser lens 25 and the ferrule 32 functions as waterproof means, even a step portion that is not close to the optical connecting portion C functions as waterproof means by allowing the step portion to have the largest diameter. However, when the optical transmitting unit 100 is used in the endoscope 2, it is preferred that the outside diameter of the metal case 23 be as small as possible, and it is difficult, in terms of design, to increase the difference in outside diameter between the step portions 23a, 23b, 23c, 23d, 23e, 23f, and 23g. Thus, when a step portion that is not close to the optical connecting portion C is used as waterproof means by allowing the step portion to have the largest diameter, if variations occur due to the dimensional tolerances of the step portions 23a to 23g, water-tightness may not be able to be ensured due to contact of other step portions with the waterproof cap 10. Therefore, the step portion 23a closest to the optical connecting portion C has the largest diameter so as to contact the inner surface of the waterproof cap 10 along an entire circumference thereof, and thereby serves as waterproof means for ensuring water-tightness. With this configuration, the water-tightness of the optical connecting portion C can be securely ensured while suppressing an increase in the size of the metal case 23.

Although in the first embodiment the optical transmitting unit 100 and the endoscope system 1 including the optical transmitting unit 100 are described, in an optical receiving unit, too, that converts an optical signal into an electrical signal and that is disposed at any of the components of the endoscope system 1, by allowing the optical receiving unit to have the same configuration as the optical transmitting unit 100, the water-tightness of an optical connecting portion can be ensured.

In addition, although in the first embodiment, the cylindrically shaped waterproof cap 10 having substantially the same diameter from an opening portion to a bottom is used, the configuration is not limited thereto. A tapered shape whose diameter increases in a direction of an opening portion from a bottom may be employed. By increasing the diameter of the opening portion side, the likelihood of contact between the step portions 23b to 23g other than the step portion 23a serving as waterproof means and the waterproof cap 10 can be reduced. The waterproof cap 10 may be tapered all the way from a bottom to an opening portion; however, it is preferred to employ a cylindrical shape with the same diameter from a bottom to near a contact portion with the step portion 23a serving as waterproof means, and a tapered shape for the rest.

Second Embodiment

Figure 5:
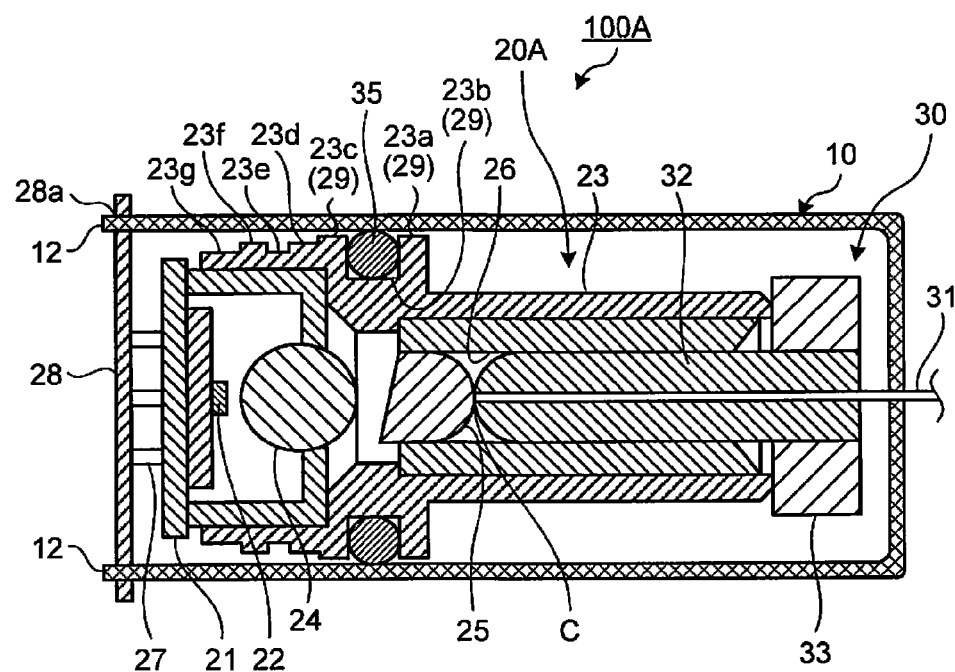
FIG. 5 is a cross-sectional view of an optical transmitting unit according to a second embodiment of the present invention.

FIG. 5 is a cross-sectional view of an optical transmitting unit according to a second embodiment of the present invention. In an optical transmitting unit 100A according to the second embodiment, waterproof means differs from the one in the first embodiment in that the waterproof means includes: a groove portion 29 formed by three continuous step portions 23a to 23c that are the closest step portions to an optical connecting portion C; and an O-ring 35 provided in the groove portion 29.

It is preferred that the outside diameter of the O-ring 35 provided in the groove portion 29 be larger than the inside diameter of a waterproof cap 10 and the outside diameters of step portions 23a to 23g. Since the outside diameter of the O-ring 35 is larger than the inside diameter of the waterproof cap 10 and the outside diameters of the step portions 23a to 23g, only the O-ring 35 contacts an inner surface of the waterproof cap 10, and thereby to ensure the water-tightness of the optical connecting portion C.

In the optical transmitting unit 100A of the second embodiment, the waterproof cap 10 may have a cylindrical shape with substantially the same diameter from an opening portion to a bottom, or may have a tapered shape whose diameter increases in a direction of an opening portion from a bottom. In addition, in an optical receiving unit, too, that converts an optical signal into an electrical signal and that is disposed at any of the components of an endoscope system 1, as with the optical transmitting unit 100A, by forming waterproof means by a groove portion composed of three continuous step portions that are the closest step portions from an optical connecting portion; and an O-ring provided in the groove portion, the water-tightness of the optical connecting portion can be ensured.

Third Embodiment

Figure 6:
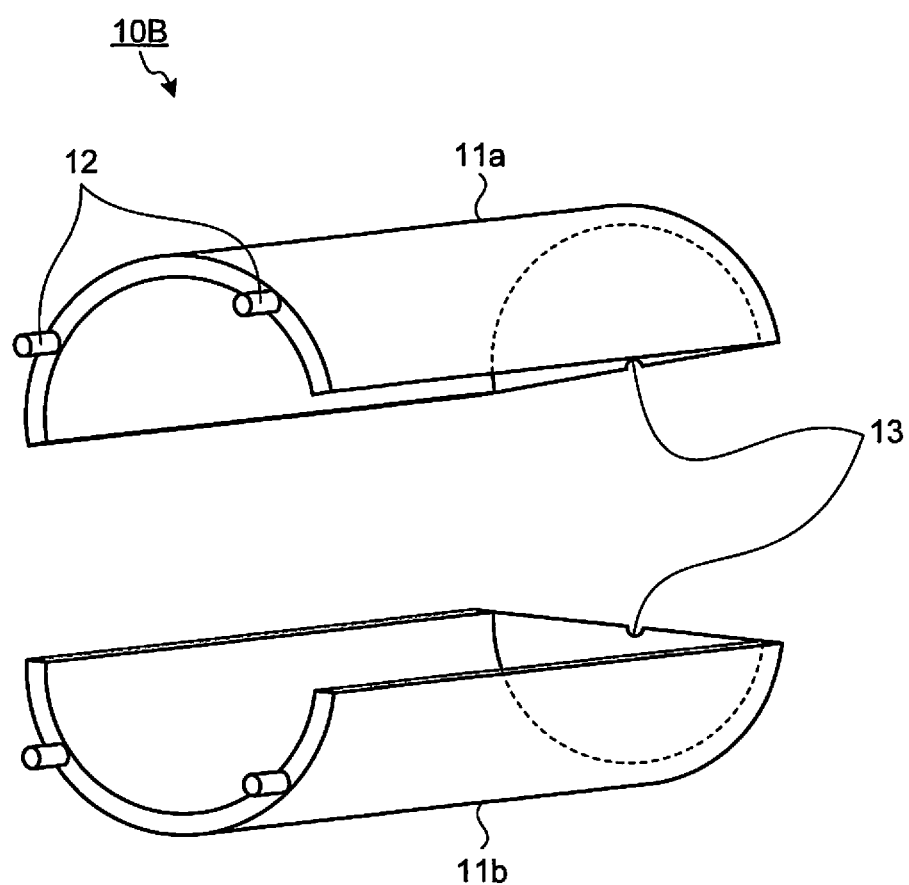
FIG. 6 is a diagram illustrating a waterproof cap according to a third embodiment of the present invention.

FIG. 6 is a diagram illustrating a waterproof cap according to a third embodiment of the present invention. In the third embodiment, a waterproof cap 10B is formed by combining two main body portions 11a and 11b which are divided in a height direction.

In the waterproof cap 10B, an optical transmitting module and an optical connector which are connected to each other are capped by the main body portions 11a and 11b in upper and lower directions, and end faces are bonded with an adhesive. Alternatively, the main body portions 11a and 11b may be formed of a thermoplastic material or a material that is softened by ultraviolet radiation, and connecting portions may be heated or subjected to ultraviolet irradiation for melt connection. Since the waterproof cap 10B is formed by the two divided main body portions 11a and 11b, even when the optical transmitting module and the optical connector are being attached to each other, placement of the waterproof cap 10B is facilitated.

In the third embodiment, by covering an optical transmitting module 20 (first embodiment) in which the closest step portion from an optical connecting portion C is used as waterproof means, or an optical transmitting module 20A (second embodiment) whose waterproof means is formed from a groove portion composed of three continuous step portions that are the closest step portions from an optical connecting portion C; and an O-ring provided in the groove portion, by the main body portions 11a and 11b and connecting the main body portions 11a and 11b together, the water-tightness of the optical connecting portion C can be ensured.

According to some embodiments, a metal case has a plurality of step portions with different outside diameters, one of the plurality of step portions closest to an optical connecting portion has the largest diameter, and the one of the plurality of step portions closest to the optical connecting portion is brought into contact with an inner surface of a waterproof cap covering the optical connecting portion along an entire circumference. With this configuration, even when an optical transmitting and receiving unit is used in an endoscope or the like and the endoscope is damaged, the water-tightness of the optical connecting portion can be ensured.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical transmitting and receiving unit comprising:
an optical transmitting and receiving module having one or more of a light emitting element and a light receiving element and having a metal case that stores the light emitting element or the light receiving element;
an optical connector having a ferrule for holding an optical fiber and having a flange portion provided at one end of the ferrule, the ferrule being inserted into a sleeve of the metal case to connect the optical connector with the optical transmitting and receiving module; and
a tubular waterproof cap that has a bottom, with one end open and the other end closed, and caps the optical connector to seal an optical connecting portion between the optical connector and the optical transmitting and receiving module in a watertight manner, wherein
the metal case has a plurality of step portions with different outside diameters, and
one of the plurality of step portions closest to the optical connecting portion contacts an inner surface of the waterproof cap along an entire circumference thereof.

2. The optical transmitting and receiving unit according to claim 1, wherein an outside diameter of the one of the plurality of step portions closest to the optical connecting portion is larger than outside diameters of the other of the plurality of step portions and larger than an inside diameter of the waterproof cap.

3. The optical transmitting and receiving unit according to claim 1, wherein the waterproof cap has a connecting portion to a substrate to be connected on a side of the open end of the waterproof cap.

4. The optical transmitting and receiving unit according to claim 1, wherein the waterproof cap is a combination of two main body portions divided in a height direction of the waterproof cap.

5. An optical transmitting and receiving unit comprising:
an optical transmitting and receiving module having one or more of a light emitting element and a light receiving element and having a metal case that stores the light emitting element or the light receiving element;
an optical connector having a ferrule for holding an optical fiber and having a flange portion provided at one end of the ferrule, the ferrule being inserted into a sleeve of the metal case to connect the optical connector with the optical transmitting and receiving module; and
a tubular waterproof cap that has a bottom, with one end open and the other end closed, and caps the optical connector to seal an optical connecting portion between the optical connector and the optical transmitting and receiving module in a watertight manner, wherein
the metal case has a plurality of step portions with different outside diameters,
an O-ring is provided in a groove portion closest to the optical connecting portion, and
the O-ring contacts an inner surface of the waterproof cap along an entire circumference thereof.

6. The optical transmitting and receiving unit according to claim 5, wherein an outside diameter of the O-ring is larger than an inside diameter of the waterproof cap and outside diameters of the plurality of step portions.

7. The optical transmitting and receiving unit according to claim 5, wherein the waterproof cap has a connecting portion to a substrate to be connected on a side of the open end of the waterproof cap.

8. The optical transmitting and receiving unit according to claim 5, wherein the waterproof cap is a combination of two main body portions divided in a height direction of the waterproof cap.

* * * * *